US008628835B2

(12) United States Patent
McDuff

(10) Patent No.: US 8,628,835 B2
(45) Date of Patent: Jan. 14, 2014

(54) LOCALIZED REINFORCEMENT FOR LAMINATED PANEL E.G., FOR A PROSTHESIS

(75) Inventor: Rodrigue McDuff, St-Bruno (CA)

(73) Assignee: Fiducie de capital IDEO, St-Bruno-de-Montarville (CA)

( * ) Notice: Subject to any disclaimer, the term of this patent is extended or adjusted under 35 U.S.C. 154(b) by 0 days.

(21) Appl. No.: 13/156,511

(22) Filed: Jun. 9, 2011

(65) Prior Publication Data
US 2011/0307081 A1    Dec. 15, 2011

Related U.S. Application Data

(60) Provisional application No. 61/352,993, filed on Jun. 9, 2010.

(51) Int. Cl.
*A61F 2/66*    (2006.01)
*B32B 3/00*    (2006.01)
*B29C 70/02*   (2006.01)

(52) U.S. Cl.
USPC ............................................. 428/76; 428/68

(58) Field of Classification Search
USPC ....................................................... 428/76, 68
See application file for complete search history.

(56) References Cited

U.S. PATENT DOCUMENTS 5,667,864 A * 9/1997 Landoll .......................... 428/74

\* cited by examiner

*Primary Examiner* — Brent O'Hern
(74) *Attorney, Agent, or Firm* — Norton Rose Fulbright Canada LLP

(57) ABSTRACT

A laminated panel is formable into a prosthesis. An outer layer of the panel has upper and lower surfaces, and is made of a thermoformable material. An inner layer of the panel has upper and lower surfaces, and is positioned relative to the outer layer such that the lower surface of the inner layer faces the upper surface of the outer layer. At least one reinforcement member has an area representing at most part of the upper surface of the outer layer. The reinforcement member is encapsulated between the inner and outer layers at a selected position relative to the outer layer, locally reinforcing the laminated panel. A prosthesis for a foot of a user made from a laminated panel, and a method of forming a prosthesis for a foot of a user with an outer layer of thermoformable material and an inner layer, are also described.

6 Claims, 3 Drawing Sheets

US 8,628,835 B2

LOCALIZED REINFORCEMENT FOR LAMINATED PANEL E.G., FOR A PROSTHESIS

CROSS-REFERENCE TO RELATED APPLICATION

The present patent application claims priority on U.S. provisional Patent Application No. 61/352,993, filed on Jun. 9, 2010, and incorporated herein by reference.

BACKGROUND OF THE INVENTION

1. Field of the Invention

The present invention generally relates to laminated panels and to a lamination process and, more particularly but not exclusively, to a process for laminating various layers into a laminated panel with localized reinforcement, for subsequent use of the laminated panel as a component of a foot prosthesis, or the like.

2. Background Art

Laminated panels are found in a plurality of products. Laminated panels typically consist of a plurality of layers, each layer being part of the laminated panels for given properties. Therefore, laminated panels are used as an alternative to well known materials, such as leather and polymers (e.g., vinyl), in the fabrication of goods.

The layers constituting laminated panels are chosen for various properties that will suit the subsequent use of the product. For instance, layers having properties such as resilience, impermeability, strength, shock absorption and softness are combined to be laminated into panels that will have selected characteristics.

A particular characteristic of some laminated panels is the ability to be formed into rounded shapes, with appropriate conditions such as a fusing temperature. The resulting laminated panels have a smooth surface. The characteristic, combined to the fact that various part of a same laminated panel may have different features in accordance with the materials used in specific layers, opens the door to other applications, such as the customizable prosthesis.

SUMMARY OF INVENTION

It is therefore an aim of the present invention to provide a laminated panel for prostheses that addresses issues associated with the prior art.

Therefore, in accordance with the present invention, there is provided a laminated panel formable into a prosthesis comprising: an outer layer having an upper surface and a lower surface, the outer layer be made of a thermoformable material; an inner layer having an upper surface and a lower surface, the inner layer positioned relative to the outer layer such that the lower surface of the inner layer faces the upper surface of the outer layer; and at least one reinforcement member having an area representing at most part of the upper surface of the outer layer, the reinforcement member being encapsulated between the inner and outer layers at a selected position relative to the outer layer so as to locally reinforce the laminated panel.

Further in accordance with the present invention, there is provided a prosthesis for a foot of a user made from a laminated panel comprising: an outer layer having an upper surface and a lower surface, the outer layer being made of thermoformable material, the lower surface of the outer layer being adapted to interface the prosthesis with an interior of an item of footwear; an inner layer having an upper surface and a lower surface, the inner layer positioned relative to the outer layer such that the lower surface of the inner layer faces the upper surface of the outer layer, the upper surface of the inner layer being adapted to interface the prosthesis with the foot of a user; and at least one reinforcement member having an area representing at most part of the upper surface of the outer layer, the reinforcement member being encapsulated between the inner and outer layers at a selected position relative to the prosthesis so as to locally reinforce the laminated panel in an arch region of the foot; whereby the laminated panel is thermoformed into the shape of the foot of the user.

Still further in accordance with the present invention, there is provided a method of forming a prosthesis for a foot of a user with at least an outer layer of thermoformable material and an inner layer, comprising: superposing the outer layer and the inner layer; locally positioning a reinforcement member with respect to the outer layer for the reinforcement member to eventually be aligned with an arch region of the foot; heating the outer layer to fuse a portion of the fusible layer; and compressing the outer layer with the inner layer to encapsulate the reinforcement member therebetween to form a prosthesis blank.

BRIEF DESCRIPTION OF THE DRAWINGS

Having thus generally described the nature of the invention, reference will now be made to the accompanying drawings, showing by way of illustration a preferred embodiment thereof and in which.

DESCRIPTION OF THE PREFERRED EMBODIMENTS

Figure 1:
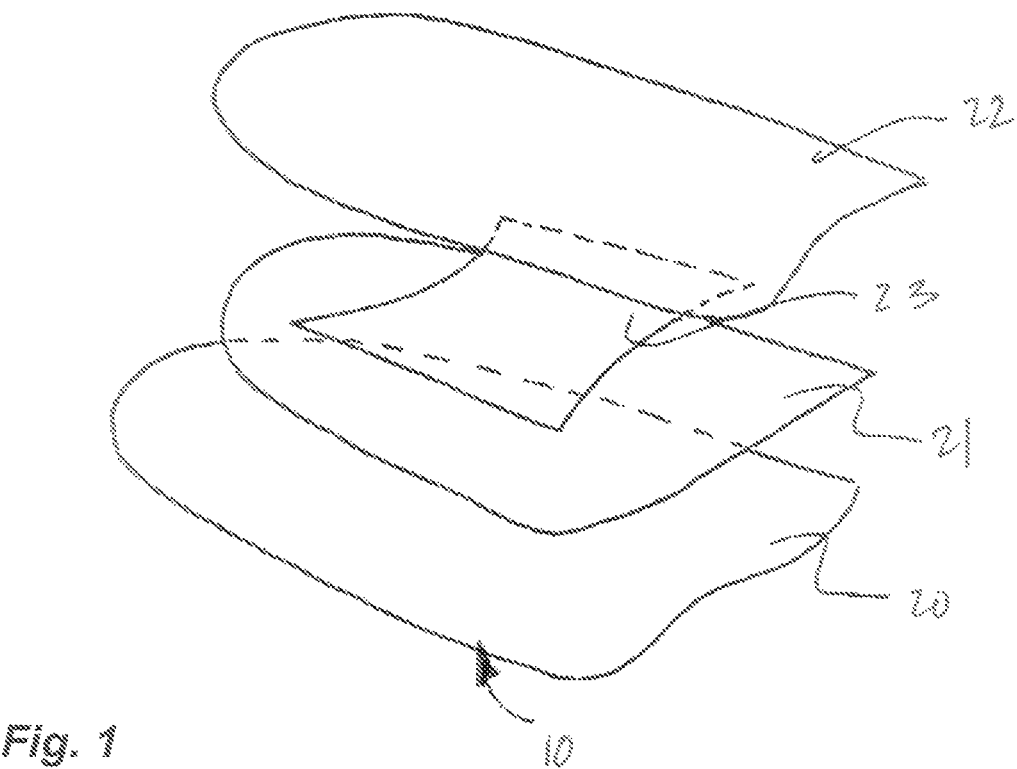
FIG. 1 is a exploded view of a laminated panel with localized reinforcements, constructed in accordance with a preferred embodiment of the present invention.
Figure 2:
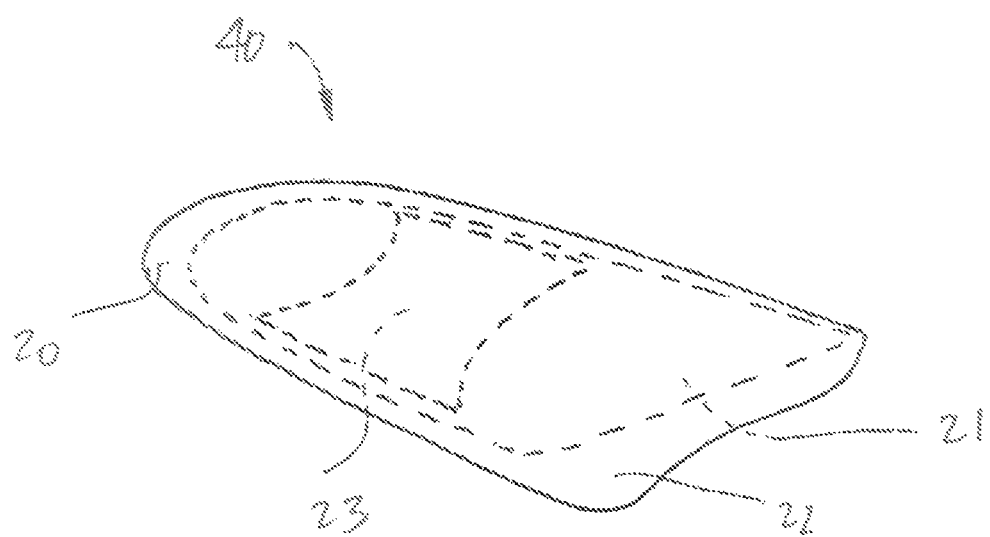
FIG. 2 is a perspective view of the laminated panel with localized reinforcements of FIG. 1.

Referring now to the drawings, and more particularly to FIGS. 1 and 2, a laminated panel in accordance with a preferred embodiment is generally shown at 10. The laminated panel 10 is illustrated in a precut shape of a blank prosthesis, of the type used as an interface between a shoe and the foot of a user, for instance to support the arch and heel of the foot. It is pointed out that the laminated panel can be generically produced in any appropriate shape dependent on the use of the laminated panel, or may be laminated in a generic shape to then be cut into a selected shape such as the prosthesis blank of FIGS. 1 and 2.

Referring to FIG. 1, the laminated panel 10 is exploded to illustrate its various layers. The laminated panel 10 has an outer layer 20, a core 21 and an inner layer 22. Although the laminated panel 10 is illustrated as having three layers, fewer or more layers could be provided in the laminated panel 10.

In the foot prosthesis embodiment, the outer layer 20 is typically the one that contacts the inner sole of the shoe/boot, and is chosen accordingly. For instance, the outer layer 20 is a carbon fiber sheet, with a thermoformable material, such as Surlyn™, laminated thereto. Other materials are also considered, such as a plastic, nylon, a felt, or the like, that have a selected finish. In the embodiment in which the outer layer 20 is a combination of carbon fiber and Surlyn™ laminated to one another, the Surlyn™ may be transparent, and its thickness is selected as a function of the desired rigidity of the laminated panel 10.

The core 21 is chosen as a function of the use of the laminated panel 10. For instance, structural rigidity is typically required after deformation of the laminated panel 10, whereby a cellulose fiber may be used. A combination of cellulose fiber impregnated with surface adhesives (e.g., ethylene vinyl acetate) is suited to be formed into given shapes, and maintain its new shape while having a sufficient strength to support the loads.

Alternatively, if padding is required, the core 21 may be a foam polymer. Expanded polymers are also well suited to be used as the material of the core 21. Expanded polymers considered for the core 21 are expanded polypropylene (i.e., EPP), expanded polyethylene (i.e., EPE), Arcel™, or the like.

The inner layer 22 is typically exposed in an interior of the boot, whereby the material used is typically a fabric or like soft material or textile. For instance, a polyester fabric is typically used as the inner layer 22. Depending on the types of material used for the core 21 and the inner layer 22, an adhesive may be required to suitably secure the core 21 to the inner layer 22. The use of polyester for the inner layer 22 allows the secure bonding of any additional layer thereon, in the event that additional layers are required.

Referring to FIGS. 1 and 2, a reinforcement member 23 is positioned at a specific location in the laminated panel at which reinforcement is required, between the lower surface of the inner layer 22 and the upper surface of the core 21. As the example of FIGS. 1 and 2 represents a prosthesis for the arch region of the foot (i.e., longitudinal and transverse), reinforcement is typically required in the arch region of the foot. Accordingly, the reinforcement member 23 is provided in this locations so as to increase the structural strength of the laminated panel 10 in these specific areas.

The type of material used for the reinforcement members 23 is selected as a function of the contemplated function of the reinforcement member. According to an embodiment, cellulose fiber is used once more, with or without a surface adhesive, in addition to the cellulose fiber of the core 21. Other materials, such as polymeric materials, polymeric foams or expanded polymers may be used.

In order to be laminated, the pre-cut components of the laminated panel 10 are superposed above one another as required as shown in FIGS. 1 and 2, with applicable adhesives if required (e.g., thermofusible glue film). It may be required to temporarily use jigs or tape to maintain the various layers in the desired position relative to one another.

A lamination press then applies pressure (by compression) to the laminated panel 10, and transfers heat simultaneously. The combination of heat and pressure will result in the lamination of the layers 20, 21 and 22 to one another, encapsulating the localized reinforcements member 23. The heat and pressure from the press will result in the interconnection of the outer layer 20, the core 21 and the inner layer 22, whether through the use of adhesive or compatible reactions between the materials.

Suitable press settings will ensure that the laminated panel 10 exiting the press has a generally uniform thickness, notwithstanding the presence of reinforcement members 23. More specifically, as the layers 20, 21 and or 22 fuse under the action of heat from the press, the pressure of the press will equalize the thickness of the laminated panel 10. A cooling period may be required prior to the removal of the laminated panel from the press. As a result, the prosthesis blank is obtained in a generally flat state.

Figure 4:
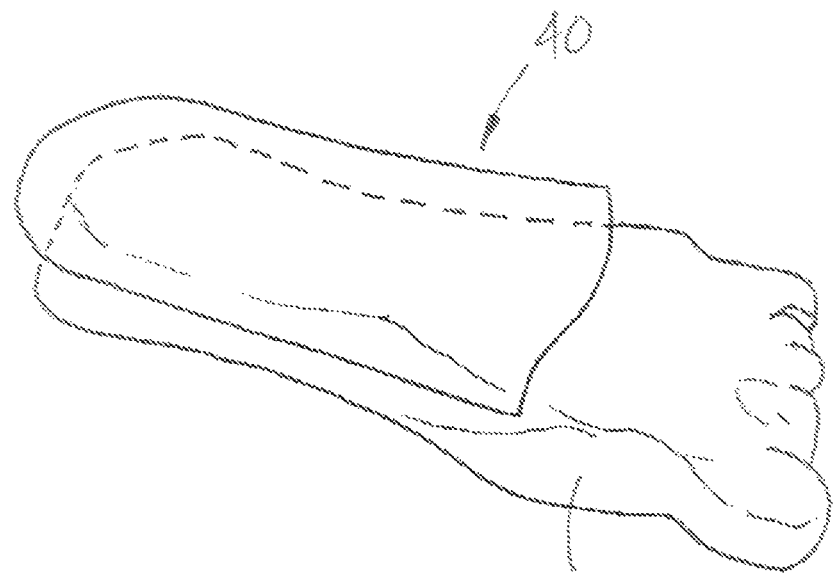
FIG. 4 is a process view of the laminated panel of FIG. 1 relative to a model of a foot.
Figure 5:
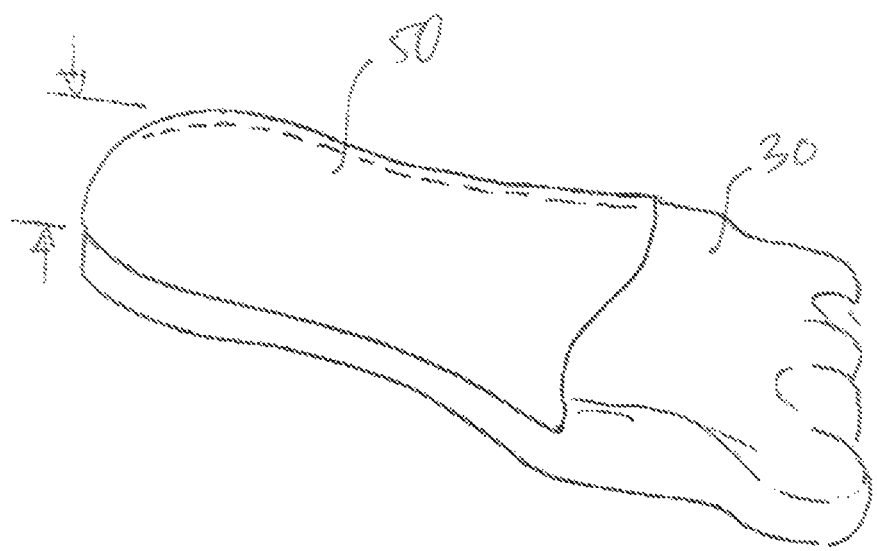
FIG. 5 is a perspective view of the laminated panel and model of FIG. 4, with the laminated panel being thermoformed into a prosthesis.

The prosthesis blank may then be thermoformed into the appropriate shape, to be customized for a given patient. The various prosthesis blanks may be selected as a function of their size, and of the required characteristics of the prosthesis, for instance in terms of structural rigidity, and shock absorption. As shown in FIGS. 4 and 5, a foot model 30 modeled off a patient) may be used for the thermoforming process, in which the prosthesis blank 40 is heated to soften its various layers. The blank 40 is deformed into conforming to the shape of the foot model 30, by the application of appropriate pressure. According to an embodiment, the foot model 30 has vacuum ports to produce a suction common to thermoforming processes. Alternatively, a pressure may be manually or automatically applied onto the outer layer 20 to press the softened blank 40 onto the foot model 30.

Figure 3:
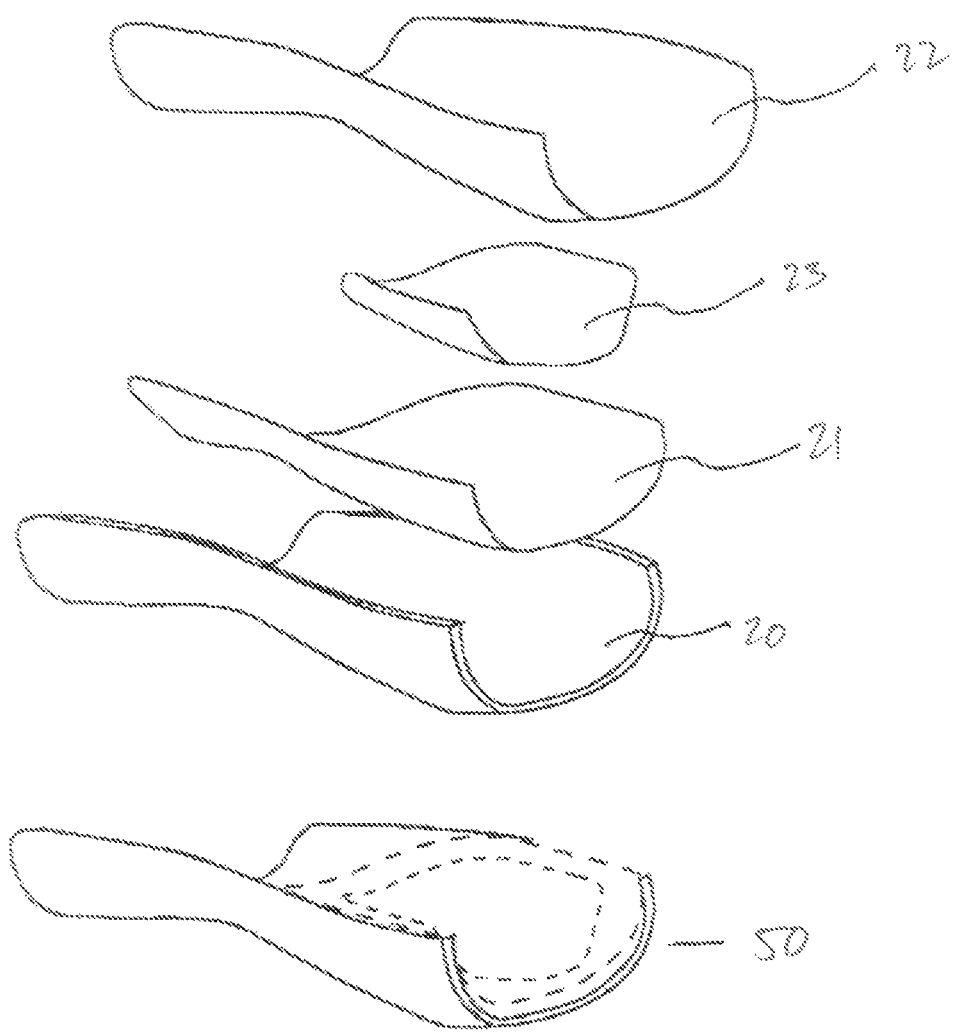
FIG. 3 is an assembly view of the laminated panel with localized reinforcements as thermoformed into a prosthesis.

There results the prosthesis 50 as shown in FIGS. 3 and 5, customized to the patient's foot. The prosthesis 50 may therefore have a greater density of material at the areas of the foot requiring additional support (e.g., arch region). Moreover, the thermoforming process may be performed in such a way that the thickness of the prosthesis 50 is lesser in some areas (e.g., forefoot, heel, the contact portions of foot). The prosthesis 50 may have a high strength to thickness ratio, in accordance with the specifics of the materials used. The thinnest of the prosthesis 50 may lessen the impact of any loss of comfort due to the presence of a prosthesis in a shoe, at the zones of junction between shoe and prosthesis 50.

It may be required to perform other finishing steps to the prosthesis 50. Such finishing steps are typically manual steps to embellish the prosthesis 50, and may include any of cutting and sanding.

Referring to FIG. 3, it is observed that the periphery of the laminated panel 10 is constituted from the outer layer 20 and the inner layer 22. Accordingly, the thickness at the periphery of the laminated panel 10 may be thinner than in its center. This is particularly useful to prevent any discomfort by a thick junction between shoe and prosthesis.

The invention claimed is:

1. A panel formable into a prosthesis comprising:
    an outer layer having an upper surface and a lower surface, the outer layer being made of a thermoformable material;
    an inner layer having an upper surface and a lower surface, the inner layer positioned relative to the outer layer such that the lower surface of the inner layer faces the upper surface of the outer layer;
    at least one reinforcement member having an area representing at most part of the upper surface of the outer layer, the reinforcement member being encapsulated between the inner and outer layers at a selected position relative to the outer layer so as to locally reinforce the panel;
    a laminated condition in which at least the outer layer, the inner layer and the reinforcement member are laminated into a laminated panel having a generally uniform thickness; and
    a thermoformed condition in which the laminated panel is thermoformed to retain a customized shape.

2. The panel according to claim 1, further comprising a core encapsulated between the inner and outer layers and extending generally over a substantial portion of the upper surface of the upper surface of the outer layer.

3. The panel according to claim 2, wherein the core and the at least one reinforcement member consist of a cellulose fiber material.

4. The panel according to claim 3, wherein the cellulose fiber material of at least one of the core and the reinforcement member is pre-impregnated with an adhesive.

5. The panel according to claim 1, wherein the outer layer has a sheet of carbon fiber.

6. The panel according to claim 1, wherein the inner layer is made of a polyester fabric.

\* \* \* \* \*